(12) United States Patent
Reed et al.

(10) Patent No.: US 6,769,664 B2
(45) Date of Patent: Aug. 3, 2004

(54) CASTING APPARATUS FOR ELECTROPHORETIC GEL TRAY

(76) Inventors: Thomas D. Reed, 1512 Northview Ave., Cincinnati, OH (US) 45223; Arthur P. Case, 1130 Exper Dr., Park Hills, KY (US) 41011

( * ) Notice: Subject to any disclaimer, the term of this patent is extended or adjusted under 35 U.S.C. 154(b) by 229 days.

(21) Appl. No.: 09/946,245

(22) Filed: Sep. 5, 2001

(65) Prior Publication Data

US 2003/0042395 A1 Mar. 6, 2003

Related U.S. Application Data

(60) Provisional application No. 60/230,080, filed on Sep. 5, 2000.

(51) Int. Cl.[7] .............................................. B29C 39/22
(52) U.S. Cl. ........................ 249/112; 249/120; 249/158
(58) Field of Search ................................ 249/112, 120, 249/139, 155, 158, 161

(56) References Cited

U.S. PATENT DOCUMENTS

| | | | |
|---|---|---|---|
| 4,151,065 A | 4/1979 | Kaplan | 204/299 R |
| 4,588,491 A | 5/1986 | Kreisher | 204/299 |
| 4,618,408 A | 10/1986 | Malavarca | 204/299 |
| 4,830,725 A | 5/1989 | Berninger | 204/299 |
| 4,954,236 A | 9/1990 | Kushner | 204/299 |
| D315,952 S | 4/1991 | Berninger | D24/8 |
| 5,192,408 A | 3/1993 | Scott | 204/182.8 |
| 5,232,573 A | 8/1993 | Rosenvold | 204/299 |
| 5,410,412 A | 4/1995 | Gombocz | 356/417 |

Primary Examiner—James P. Mackey
Assistant Examiner—Donald Heckenberg

(57) ABSTRACT

A casting apparatus for receiving electrophoretic gel trays is disclosed. The casting apparatus includes a flat-surfaced base with upright walls at proximal and distal ends, thus forming a U-shaped chamber with open sides and top. Shafts extend parallel with the base from the outer ends of the proximal wall to supporting elements mounted between the proximal and distal walls. The bars pass through holes drilled through a moveable partitioning wall that is parallel to the end walls, and able to slide along the bars. An open-ended gel tray of varying size may be placed in the interior casting chamber formed between the sliding and distal walls. Contact between the gel tray and the casting apparatus is achieved by means of compression springs on the shafts, proximal to the sliding wall, which apply constant pressure against the sliding wall towards the gel tray and distal wall. A liquid-tight seal at each end of the gel tray is formed by means of gasket material lining the interior faces of the sliding and distal walls. A feature of the apparatus is a groove cut into the top surface of the sliding wall that facilitates its retraction, thus allowing gel trays to be rapidly placed into or removed from the casting chamber.

10 Claims, 6 Drawing Sheets

CASTING APPARATUS FOR ELECTROPHORETIC GEL TRAY

This application claims the benefit under 35 U.S.C. 119(e) of provisional application 60/230,080, filed Sep. 5, 2000.

BACKGROUND

The present invention relates in general to a casting apparatus for electrophoretic gel trays, and more particularly, to such an apparatus adapted for casting a separation medium such as agarose and polyacrylamide gel solution in an open-ended gel tray for horizontal gel electrophoresis. Application of such electrophoretic gels includes the separation and analysis of DNA, RNA, and other molecules of interest.

Electrophoresis is an analytical method widely used in research and clinical analytical processes. A variety of electrophoretic techniques are employed, including thin-layer, column, and upright slab gel electrophoresis, however, the present invention is a method for producing a gel for horizontal electrophoresis. While other substances and molecules may be subjected to horizontal electrophoresis, this technique is most widely used to separate and analyze nucleic acids such as DNA or RNA molecules. The source of these molecules may be tissue or cells from living or dead organisms, or from cultured cells. Molecules of interest also may be synthetically generated by PCR, RT-PCR, oligo-nucleotide synthesis, or other laboratory methods.

The general principle of electrophoresis is the movement of molecules in a mixture through a medium capable of retarding the movement of the molecules as a function of molecular weight, charge, size or conformation. The driving force is most frequently an applied electrical field through the medium. The typical embodiment of this medium is an agarose gel of a predetermined thickness submerged in a buffer capable of transferring an electrical charge. The ends of the gel are generally open to the buffer to allow the electrical current to enter one end of the gel, pass through the gel, and exit the other end through the buffer. In this manner, molecules are compelled to move through the gel and may be separated from each other.

In order to cast a gel, the ends of a gel tray that are open during the electrophoresis process must be temporarily blocked during the casting process so as to form a mold. A second toothed-mold called a comb is placed within the gel tray mold so that tooth-shaped wells will be formed in the gel. A solution of agarose, acrylamide, or other suitable media is poured into the gel tray mold and allowed to cool and polymerize. When the gel has polymerized, the temporary blocks are removed from the ends of the tray, and the comb is lifted from the gel. The gel and its supporting gel tray are transferred to an electrophoresis box and submerged in electrophoretic buffer. Samples of mixtures to be analyzed are placed in the wells and subjected to electrophoresis.

Despite the variety of commercially available gel casting apparatuses, the most widely used method for blocking the open ends of the tray is still the manual application of tape. Persistence of the use of tape is due to lack of a versatile apparatus that can accommodate a wide variety of gel tray and/or comb sizes and shapes, as well as failure of currently available products to hold a reliably liquid-tight seal. While taping the ends of the trays is generally satisfactory and will usually work with most gel trays, there are some gel tray designs with base pieces extending beyond the side walls, thus making it difficult to reliably seal the ends. However, this is not a problem limited to those certain gel tray designs. Tape adhesion can fail with a gel tray of any design, since the heat of liquid agarose can cause loss of adhesion and leakage when the liquid agarose is poured into the taped tray. Heat-resistant tape of a suitable adhesive quality is fairly costly, and over time, can amount to a considerable expense. While some commercially available casting systems seal adequately, they require the use of a specific gel electrophoresis box and gel tray system and cannot accommodate trays and/or combs from other manufacturers. Furthermore, high temperatures of liquid agarose can cause temporary or permanent warping of the gel tray and/or gasket pieces in some systems and compromise the integrity of the seal. Some systems also require the use of locking bolts or other loose parts that may break or be lost easily, further decreasing the utility of such systems. Currently, there is no quick and easy way to reliably block the ends of a wide variety of gel tray styles and sizes using a single apparatus.

SUMMARY OF THE INVENTION

It is broadly an object of the present invention to provide a casting apparatus for electrophoretic gel trays specifically adapted for nucleic acid electrophoresis systems which provides a liquid-tight seal for the purpose of casting an electrophoretic gel of a predetermined thickness. It is also an object of the present invention to provide a rapid means of preparing an open-ended gel tray for the purpose of casting an electrophoretic gel, the function of which is unaffected by the heat of a typical gel solution.

The casting apparatus described in this application rapidly and reliably creates a liquid-tight seal at each end of a gel tray. The casting apparatus can accommodate gel trays of varying sizes, including those originally designed to work only as components within specially designed systems. The design of the casting apparatus does not interfere with placement of combs within gel trays. Unlike tape, the structure of the present invention is durable and reusable. The high heat of a typical gel solution does not affect the performance of the present invention. The versatility and reusability make the present invention more useful and economical than any other system in the prior art, including the use of tape. In addition, it is compact enough to be placed in a refrigerator to enhance the formation of a gel. Furthermore, the present invention provides an easy means of rapidly removing the gel tray and gel from the casting apparatus while minimizing the risk of damaging the gel.

BRIEF DESCRIPTION OF THE INVENTION

The invention is an apparatus for casting an electrophoretic separation medium within a received gel tray having open ends. The apparatus is constructed from a U-shaped housing, made from a base-plate with upright proximal and distal walls. Shaft supports are permanently attached to the outer edge of the upper surface of the base-plate, between the proximal and distal walls. Shafts are mounted in holes drilled approximately halfway into the interior face of the proximal wall and the opposing faces of the shaft supports. The shafts pass through compression springs and holes in an upright partitioning sliding wall. The sliding wall is held parallel with the proximal and distal walls. The shafts provide a linear means of movement for the sliding wall and guidance for the compression springs. The compression springs apply constant pressure against the sliding wall such that the pressure is directed toward the distal wall. The region between the sliding and distal walls forms a casting chamber able to receive single or multiple gel trays. Gaskets lining the opposing or interior faces of the sliding and distal walls produce a liquid-tight seal at each end of a gel tray placed within the casting chamber. A groove cut into the upper surface of the sliding wall permits the user to retract the sliding wall toward the proximal wall with one hand. When the sliding wall is retracted, a gel tray may be rapidly and easily placed into or removed from the casting chamber.

DRAWING FIGURES

Figure 1:
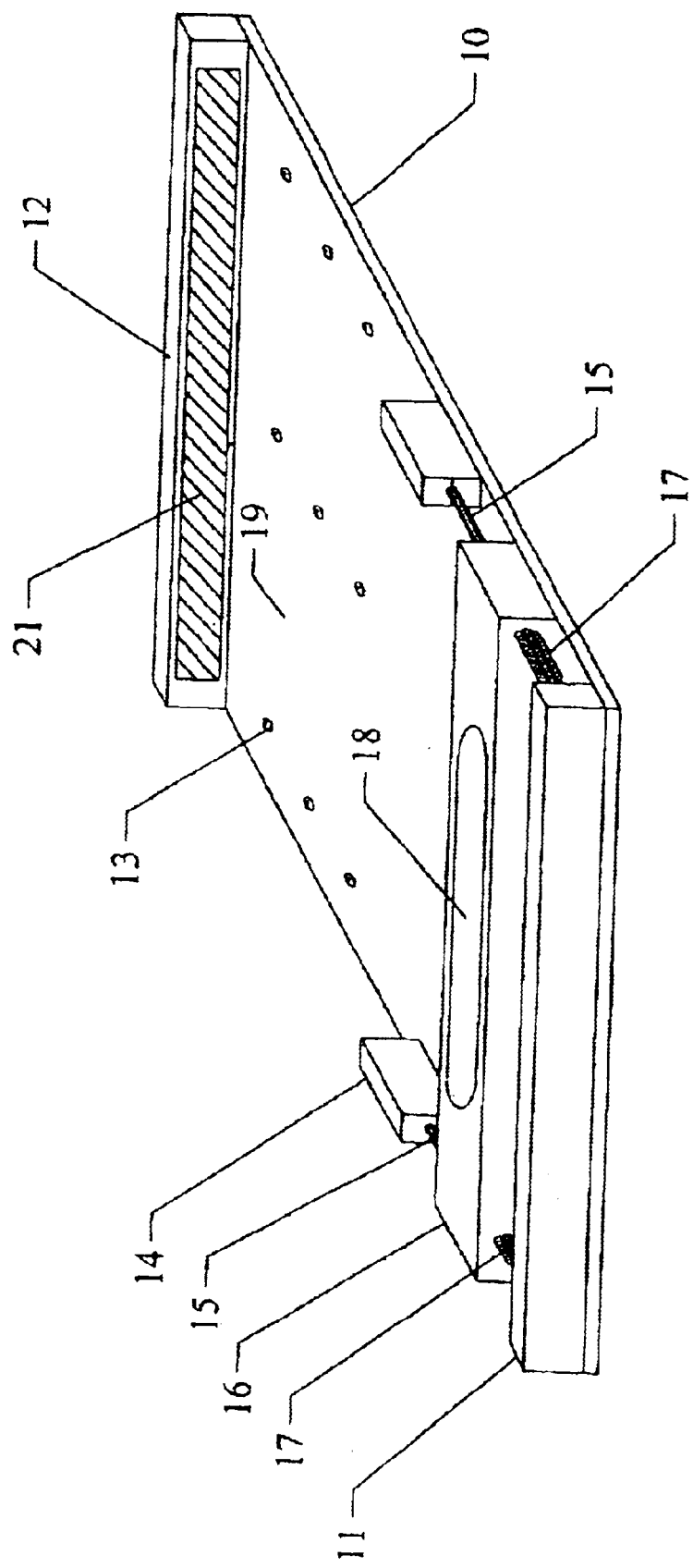
FIG. 1 is a perspective view of the present invention, which is a casting apparatus for electrophoretic gels.

REFERENCE NUMERALS IN DRAWINGS 10 base-plate
11 proximal wall
12 distal wall
13 alignment hole
14 shaft support
15 shaft
16 sliding wall
17 compression spring
18 groove
19 casting chamber
20 peg
21 gasket
22 shaft housing hole
23 screw housing

DETAILED DESCRIPTION OF THE INVENTION

The above description, as well as further objects, features and advantages of the present invention will be more fully understood by reference to the following detailed description of a presently preferred but nonetheless illustrative casting apparatus for an electrophoretic gel tray.

FIG. 1: Perspective View of Casting Apparatus

FIG. 1 is a perspective view of the present invention, which is a casting apparatus for electrophoretic gels. The casting apparatus is constructed from a U-shaped housing formed by rectangular base-plate 10 and upright walls mounted on the proximal and distal ends of base-plate 10. Proximal wall 11 is mounted permanently to base-plate 10 by mechanical means such as screws passing through base-plate 10 up into proximal wall 11, or by means of an adhesive. Distal wall 12 is mounted by means of pegs 20 (see FIGS. 2 and 4) on the undersurface of distal wall 12, which correspond to rows of alignment holes 13 drilled into base-plate 10. In the embodiment illustrated, three pegs 20 correspond to either of two rows of three alignment holes 13. The arrangement of alignment holes 13 allows distal wall 12 to be positioned at varying distances from proximal wall 11, while retaining a parallel orientation to proximal wall 11. Shaft supports 14 are mounted on both sides of the upper surface of base-plate 10 along the outer edges and between proximal wall 11 and distal wall 12. Shafts 15 are fixed between proximal wall 11 and supports 14 by means of holes drilled approximately halfway into the interior side of proximal wall 11 and the ends of each support 14 facing proximal wall 11. Partitioning sliding wall 16 is mounted on the casting apparatus by means of shaft housing holes 22 (see FIG. 3) drilled completely through the ends of sliding wall 16. Shafts 15 thus pass through housing holes 22 in sliding wall 16 and direct its linear movement along shafts 15. Shafts 15 also pass through compression springs 17 located between proximal wall 11 and sliding wall 16. Shafts 15 also guide the movement of springs 17. Springs 17 apply pressure against sliding wall 16 towards distal wall 12. Groove 18 is cut into the top surface of sliding wall 16 to a depth sufficient to allow the user to place the fingertips of one hand into groove 18. The region between sliding wall 16 and distal wall 12 is referred to as casting chamber 19. Casting chamber 19 can vary in size, according to placement of distal wall 12 in mounting holes 13 and the width and length of base plate 10, but remains within the area circumscribed by distal wall 12, sliding wall 16, and the pair of shaft supports 14. The interior faces of sliding wall 16 and distal wall 12 are covered with gasket material 21.

Figure 2:
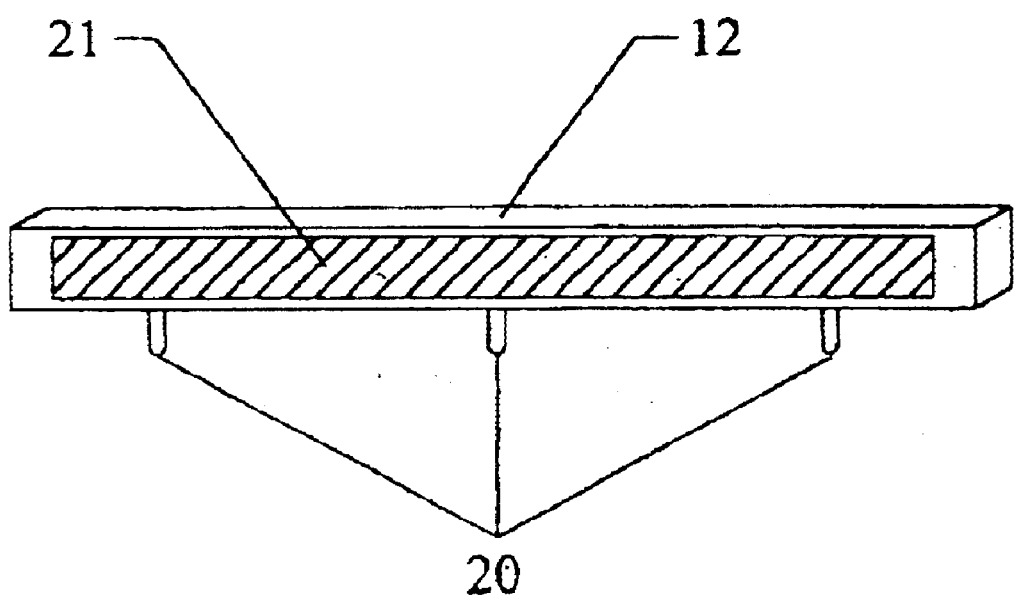
FIG. 2 is a side view of the distal wall element, showing the gasket-lined interior face and the arrangement of pegs on the underside.

FIG. 2: Side View of Distal Wall 12

FIG. 2 is a side view of distal wall 12, with the interior face in the foreground. The arrangement of pegs 20 on the underside of distal wall 12 is shown. Holes to fit pegs 20 are drilled into the underside of distal wall 12, and pegs are permanently installed using an adhesive. The size and placement of pegs 20 correspond with alignment holes 13 (illustrated in FIGS. 1 and 6). Pegs 20 mate with alignment holes 13 and allow distal wall 12 to be securely mounted at varying distances from sliding wall 16 in order to accommodate gel trays of various sizes. Gasket 21 is applied to the interior face of distal wall 12 for the purpose of creating a liquid-tight seal against the end of a gel tray during the gel-casting process.

Figure 3:
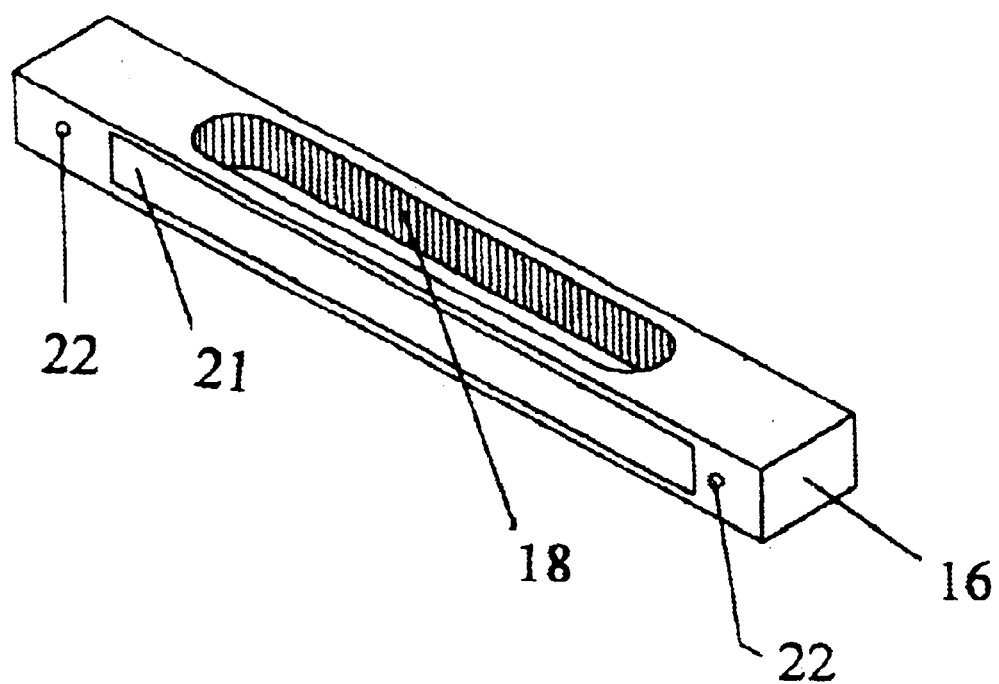
FIG. 3 is a perspective view of the partitioning sliding wall with a groove cut into the top surface and holes for mounting the sliding wall on a pair of shafts.

FIG. 3: Perspective view of Sliding Wall 16

FIG. 3 is a perspective view of sliding wall 16 with the interior-ace in the foreground. Groove 18 is cut into the top surface of sliding wall to a depth sufficient for the user to place the fingertips of one hand. The interior-face is lined with gasket 21 for the purpose of creating a liquid-tight seal against the end of a gel tray during the gel-casting process. Shaft housing holes 22 are drilled completely through each end of sliding wall 16, sized sufficiently to allow shafts 15 to pass through holes 22 (see FIG. 1) such that sliding wall 16 moves only in a linear direction, and cannot wiggle or tilt.

FIG. 4: Side View

Figure 4:
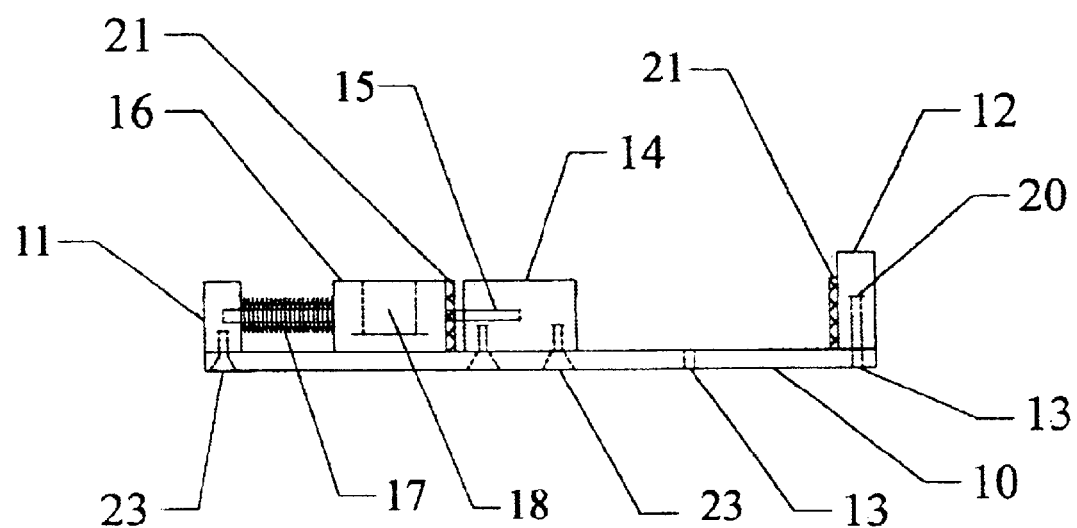
FIG. 4 is a side view of the casting apparatus showing the base-plate with the arrangement of the proximal wall, compression springs, sliding wall, shaft supports, and alignment holes for mounting the distal wall.

FIG. 4 is a side view of the casting apparatus showing base-plate 10 with the arrangement of proximal wall 11, sliding wall 16, and shaft supports 14, and distal wall 12. Shafts 15 are mounted in holes drilled approximately halfway into proximal wall 11 and shaft supports 14. Shafts 15 pass through springs 17 and sliding wall 16. The interior faces of sliding wall 16 and distal wall 12 are lined with gasket 21. The distal wall 12 may be mounted in the position illustrated, in alignment holes 13 drilled into the base-plate 10, or in an alternative row of holes 13 closer to sliding wall 16.

FIG. 5: Top View

Figure 5:
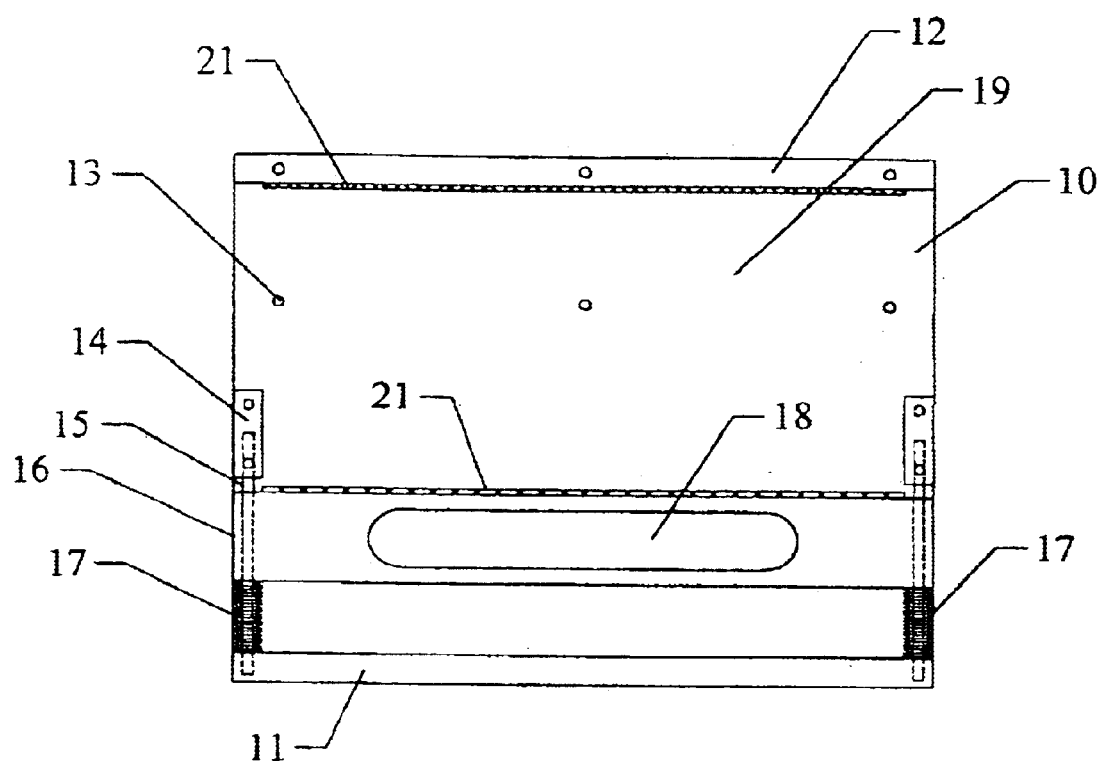
FIG. 5 is a top view of the casting apparatus, with the casting chamber in the region circumscribed by the sliding wall, shaft supports, and distal wall.

FIG. 5 is a top view of the casting apparatus. Casting chamber 19 is the region circumscribed by sliding wall 16, shaft supports 14, and distal wall 12. Shafts 15 pass through springs 17 and sliding wall 16. The embodiment illustrated has 2 rows of alignment holes 13 drilled through base-plate 10: one row in which distal wall 12 is positioned, and a parallel alternative row near the approximate center of casting chamber 19. Additional rows of alignment holes 13 may be added in alternate embodiments in order to increase or decrease the size of casting chamber 19, and thus accommodate a wider variety of gel tray sizes. Sliding wall 16 is slightly retracted toward distal wall 11.

Figure 6:
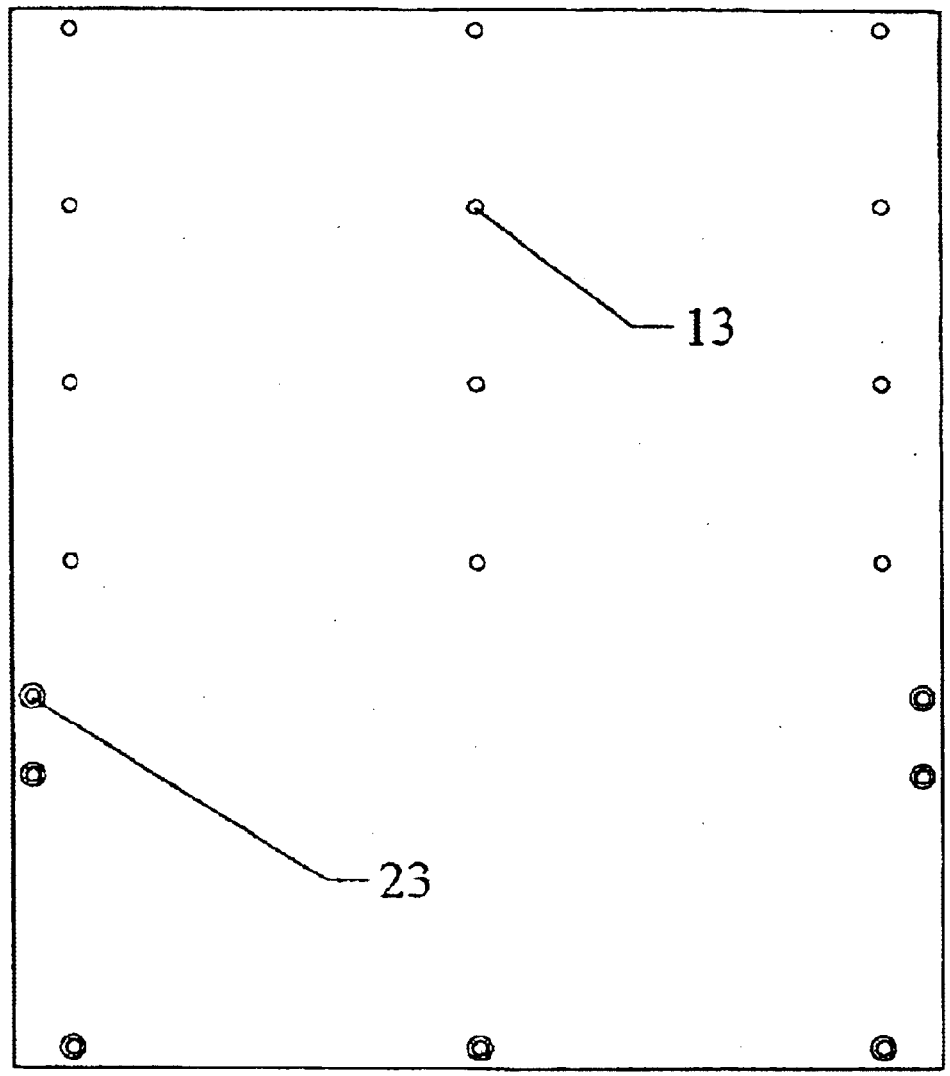
FIG. 6 is a bottom view of the casting apparatus base-plate, showing the locations of holes for mounting the proximal wall, distal wall, and shaft supports.

FIG. 6: Bottom View

FIG. 6 is a bottom view of the casting apparatus, and more specifically, of base-plate 10. This view shows the relative arrangement of mounting holes for proximal wall 11, distal wall 12, and shaft supports 14. The single circles indicate alignment holes 13 drilled through base-plate 10 for the purpose of mounting distal wall 12. In the present illustration, there are four rows of alignment holes 13. Pegs 20 (see FIG. 2) installed in the underside of distal wall 12 correspond with the size and positions of alignment holes 13. The double circles indicate holes drilled through base-plate 10 to create screw housings 23 for the purpose of mounting proximal wall 11 and shaft supports 15. Proximal wall 11 is installed at the row of screw housings 23 located at the bottom edge of base-plate 10, and one shaft support 15 is installed at each pair of screw housings 23 located along either side of base-plate 10.

Operation of the Invention

The casting apparatus (FIG. 1) is placed on a level surface, such as a laboratory bench top or table. The user determines the desired position of distal wall 12, which is dependent upon the size of the gel tray to be used, and may be limited by the number of rows of alignment holes 13 in the embodiment in use. Pegs 20 on the underside of distal wall 12 (FIG. 2) are mated with the appropriate row of alignment holes 13 in base-plate 10 (shown in FIGS. 1, 4, and 6) to achieve the desired size for casting chamber 19. The user places the fingertips of one hand into groove 18 and the thumb on the outer face of the proximal wall 11. This position allows the user to grip sliding wall 16 (FIG. 3) and compress springs 17 with a squeezing motion, thus drawing sliding wall 16 toward proximal wall 11 with one hand. With sliding wall 16 (FIG. 4) held in the retracted position, the user places a suitably sized gel tray into casting chamber 19. The bottom of the gel tray should be situated flat against the upper surface of base-plate 10, with one open end toward sliding wall 16 and the other toward distal wall 12. When a gel tray is in place within casting chamber 19, sliding wall 16 is released, and springs 17 apply pressure toward the gel tray and distal wall 16. As a result, the ends of the gel tray tightly oppose the interior walls of casting chamber 19, which are lined with gaskets 21. Constant pressure from springs 17 holds the gel tray in place and forms liquid-tight seals at each end of the gel tray. A suitable comb is positioned in the gel tray, and a prepared liquid separation medium is poured into the gel tray. The gel is allowed to cool and polymerize at room temperature or in a refrigerator. When cooling/polymerization is complete, the gel and its supporting gel tray are easily and rapidly removed from the casting apparatus by, again, grasping and squeezing groove 18/sliding wall 16 toward proximal wall 11 with fingers and thumb of one hand, and lifting the gel tray from casting chamber 19 with the other hand.

The casting apparatus described in the present application provides a durable, inexpensive means for reliably and rapidly blocking the open ends of a gel tray for a temporary interval of time. It has only one loose part (the distal wall), which remains mounted on the apparatus both during and after use, making it easier to keep all the essential elements together during storage. This reduces the chance of losing components, thus increasing the usefulness of the invention. Furthermore, it is designed to work with existing gel trays and combs from a wide spectrum of commercial sources. This universal design makes it unique; the only other universal means of blocking gel tray ends is with tape. However, tape is limited in its ability to withstand hot liquids, and must be assiduously applied in all cases. The present invention is reliably heat- and liquid-resistant, and gel trays can be easily and rapidly positioned within the casting chamber to prepare them for gel casting. Likewise, the completed gel and gel tray are easily and rapidly removed from the apparatus, with minimal risk of damage to the gel. Other systems, including removal of tape, can lead to tearing or dropping the gel-causing the user to have to recast the gel. The need to recast a gel, whether resulting from leaking gel trays or from damage to gels, is a great source of frustration and loss of time and money. The present invention reduces frustration and saves time and money when casting gels for electrophoresis.

In the preferred embodiment of the present invention, the base-plate, walls, pegs, shafts, and supports may be constructed of any durable material that is heat- and liquid-resistant. Examples of such material include, but are not limited to, fiberglass, aluminum, wood, stainless steel, or polymer plastics. Examples of suitable polymer plastics include acetyl homopolymers, fluoropolymers, polycarbonates, acrylics, polyvinyl chloride, nylon, resin compounds, laminates, and ultra high molecular weight polyethylene. The springs may be made from stainless steel, aluminum, copper, or other durable metals, as may the shafts and/or pegs. Fixed walls and supports are mounted permanently to the base-plate by mechanical means, such as screws or bolts, or by permanent adhesives. The gasket is made of rubber, silicon or other heat-resistant gasket material, preferably closed-cell, and is applied to the distal and sliding wall interior surfaces with pressure-sensitive backing or other permanent adhesive.

In an alternative embodiment, the distal wall may be permanently mounted to the base-plate in the same manner as the proximal wall and shaft supports, using mechanical means or permanent adhesives. This embodiment limits the casting chamber to only one narrow range of gel tray sizes. In yet another embodiment, multiple rows of alignment holes allow the distal wall to be placed in any of two or more positions. With multiple positions, the casting chamber can accommodate a wide range of gel tray sizes.

Hot liquid solutions of agarose, acrylamide, or other suitable electrophoretic gel media may be poured into the gel tray after placing it into the casting chamber without affecting the performance of the casting apparatus. Typically, solutions of gel media are heated to dissolve the agarose or other retarding components. The user must determine when the liquid has cooled sufficiently to permit gel casting, but must pour it before it cools to the point of polymerization. The range for pouring is typically, but not limited to, 55–70° C. Hot liquids in the upper end of this temperature range, or hotter, frequently cause leaks in gel trays sealed with tape by softening, dissolving, or otherwise weakening the adhesives. Gaskets on commercially available gel casting systems frequently fail when the hot liquids cause temporary warping of gel trays or gasket pieces. Leaking gel trays are a source of frustration and a waste of valuable time for scientists and researchers. However, the compression springs in the present invention are not affected by the heat typical of these media solutions, and so provide constant tension to maintain a liquid-tight seal at the gel tray/gasket interface. The sliding and distal walls are sufficiently thick and heat-resistant so as not to warp. Likewise, the gasket is heat- and liquid-resistant, and not affected by high temperatures typical of the gel solutions. The present invention thus provides a reliable liquid-tight seal, and extends the range of temperatures at which gels may be cast.

The cooled gel is easily removed from the casting apparatus by retracting the sliding wall with one hand and lifting the tray from the casting chamber. This is in contrast to gel trays with tape or other gasket pieces. Such materials must be pulled away or rocked loose, increasing the risk of damaging the gel. The gasket material in the present invention does not adhere to the gel, and the gel tray does not need to be tipped or rocked to remove it from the casting chamber.

A distinct advantage with the present invention is the minimal number of loose pieces required for its use. In the preferred embodiment, only the distal wall is removable, but is mounted on the base-plate during use and for storage. In the embodiment with a fixed distal wall, there are no removable pieces. Some casting systems require the user to maintain a supply of bolts, gates, dams, or gasket pieces that must be stored, assembled and disassembled for each use. Another feature of the present invention is the ability to position multiple gel trays of the same length side-by-side when the casting chamber is sufficiently wide enough to achieve this purpose. Furthermore, since the casting apparatus is not a component of a larger electrophoresis buffer chamber apparatus, it has two other distinct advantages over the prior art. First, it can be easily placed into a refrigerator to shorten the cooling time required for gel polymerization. Second, it can be used for casting additional gels even when the electrophoresis apparatus contains a gel with molecules undergoing electrophoresis.

Although the invention herein has been described with reference to particular embodiments, it is to be understood that these embodiments are merely illustrative of the principles and application of the present invention. It is therefore to be understood that numerous modifications and arrangements, including but not limited to changes that alter the size or shape of the casting chamber, may be made in the illustrative embodiments, and that such modifications and arrangements may be devised without departing from the spirit and scope of the present invention as defined by the appended claims.

What is claimed is:

1. An apparatus for casting an electrophoretic separation medium within a received tray having open ends, said apparatus comprising:
   a. a base plate with proximal and distal upright walls,
   b. a moveable partitioning wall parallel with and lying between said proximal and distal upright walls,
   c. shafts mounted between said fixed proximal wall and supports attached to said base-plate,
   d. a partitioning wall parallel mounted on said shafts, such that said partitioning wall slides along said shafts,
   e. compression springs around said shafts proximal to said partitioning wall so that pressure is directed against said partitioning wall toward said distal wall,
   f. wherein the region between said moveable partitioning wall and distal wall is a casting chamber able to receive single or multiple gel trays, and
   g. the interior wall faces of said moveable partitioning wall and said distal wall are lined with gasket material.

2. An apparatus for casting an electrophoretic separation medium within a received tray having open ends as in claim 1, wherein the shafts direct linear movement of said moveable partitioning wall and guiding said compression springs.

3. An apparatus for casting an electrophoretic separation medium within a received tray having open ends as in claim 1, wherein said distal upright wall is mounted on said base-plate by means of pegs on the underside if said distal upright wall and corresponding alignment holes in said base-plate, such that said distal upright wall may be positioned at varying distances from said proximal upright wall and said moveable partitioning wall, while maintaining a parallel orientation with respect to said proximal upright wall and said moveable partitioning wall.

4. An apparatus for casting an electrophoretic separation medium within a received tray having open ends as in claim 1, wherein a groove is cut into the upper surface of said moveable partitioning wall such that the user can place fingertips in the groove and thumb on said proximal wall, thus grasping said moveable partitioning wall and said proximal wall, and retracting said moveable partitioning wall toward said proximal wall.

5. An apparatus for casting an electrophoretic agarose gel within a received tray having open ends, said apparatus comprising:
   a. a base-plate, with proximal and distal upright walls,
   b. a moveable partitioning wall parallel with and lying between said proximal and distal upright walls,
   c. shafts mounted between said fixed proximal wall and supports attached to said base-plate,
   d. a partitioning wall parallel mounted on said shafts, such the said partitioning wall slides along said shafts,
   e. compression springs around said shafts proximal to said partitioning wall so that pressure is directed against said partitioning wall toward said distal wall,
   f. wherein region between said moveable partitioning wall and distal wall is a casting chamber able to receive single or multiple gel trays, and
   g. the interior wall faces of said moveable partitioning wall and said distal wall are lined with gasket material.

6. An apparatus for casting an electrophoretic agarose gel within a received tray having open ends as in claim 5, wherein the shafts direct linear movement of said movable partitioning wall and guiding said compression springs.

7. An apparatus for casting an electrophoretic agarose gel within a received tray having open ends as in claim 5, wherein said distal upright wall is mounted ion said base-plate be means of pegs on the underside of said distal upright wall and corresponding alignment holes in said base-plate, such that said distal upright wall may be positioned at varying distances from said proximal upright wall and said moveable partitioning wall, while maintaining a parallel orientation with respect to said proximal upright wall and said moveable partitioning wall.

8. An apparatus for casting an electrophoretic agarose gel within a received tray having open ends as in claim 5, wherein a groove is cut into the upper surface of said moveable partitioning wall such that the user can place fingertips in the groove and thumb on said proximal wall, thus grasping said moveable partitioning wall and said proximal wall, and retracting said moveable partitioning wall toward said proximal wall.

9. An apparatus for casting an electrophoretic agarose gel within a received tray having open ends, said apparatus comprising:
   a. a base-plate, with a fixed proximal wall and moveable distal upright wall, b. shafts mounted between said fixed proximal wall and supports attached to said base-plate,
c. a partitioning wall parallel mounted on said shafts, such that said partitioning wall slides along said shafts,
d. compression springs around said shafts proximal to said partitioning wall so that pressure is directs against said partitioning wall toward said distal wall,
e. wherein the region between said moveable partitioning wall and distal wall is a casting chamber able to receive single or multiple gel trays, and
f. the interior wall faces of said moveable partitioning wall and said distal wall are lined with gasket material.

10. An apparatus for casting an agarose gel with in a received tray having open ends as in claim 9, wherein said moveable distal upright wall is mounted on said base-plate by means of pegs on the underside of said distal upright wall and corresponding alignment holes in said base-plate, such that said distal upright wall may be positioned at varying distances from said proximal upright end and said moveable partitioning wall, while maintaining a parallel orientation with respect to from said proximal upright wall and said moveable partitioning wall.

* * * * *